US006214191B1

(12) United States Patent
Wiktorowicz et al.

(10) Patent No.: US 6,214,191 B1
(45) Date of Patent: *Apr. 10, 2001

(54) ELECTROPHORESIS APPARATUS AND METHOD

(75) Inventors: John E. Wiktorowicz, San Jose; Yefim Raysberg, Fremont, both of CA (US)

(73) Assignee: Lynx Therapeutics, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/448,908

(22) Filed: Nov. 23, 1999

Related U.S. Application Data

(63) Continuation of application No. 09/084,041, filed on May 22, 1998, now Pat. No. 6,013,165.

(51) Int. Cl.[7] .................................................. G01N 27/26
(52) U.S. Cl. ......................... 204/600; 204/606; 204/616
(58) Field of Search ................................... 204/450, 456, 204/459, 600, 606, 610

(56) References Cited

U.S. PATENT DOCUMENTS

| | | | | |
|---|---|---|---|---|
| 4,385,974 | * | 5/1983 | Shevitz | 204/464 |
| 4,417,967 | * | 11/1983 | Ledley | 204/406 |
| 4,904,632 | | 2/1990 | Pesek et al. | . |
| 5,017,540 | | 5/1991 | Sandoval et al. | . |
| 5,173,159 | | 12/1992 | Dutertre | . |
| 5,326,738 | | 7/1994 | Sandoval et al. | . |

(List continued on next page.)

OTHER PUBLICATIONS

Anderson, N.L., et al., "A two–dimensional gel database of rat liver proteins useful in gene regulation and drug effects studies" *Electrophoresis* 12:907–930 (1991)., Month Unknown.

Anderson, N.L., et al., "Simultaneous Measurement of Hundreds of Liver Proteins: Application in Assessment of Liver Function" *Toxicologic Pathology* 24(1) : 72–76 (1996)., Month Unknown.

Capelli, L., et al., "'Tunable' positive and negative surface charges on a capillary wall: exploiting the Immobiline chemistry" *J. Biochem. Biophys. Methods* 32:109–124 (1996).

Herbert, B.R., et al., "Two–Dimensional Electrophoresis: The State of the Art and Future Directions" *Proteome Research: New Frontiers in Functional Genomics* M.R. Wilkins, et al. (Eds.), Springer–Verlag Berlin Heidelberg New York pp. 13–33, 1997., Month unknown.

O'Farrell. P.H., "High Resolution Two–Dimensional Electrophoresis of Proteins" *J. of Biol. Chem.* 250(10) : 4007–4021 (1975)., Month Unknown.

*Primary Examiner*—Jan Ludlow
*Assistant Examiner*—Alex Noguerola
(74) *Attorney, Agent, or Firm*—Vincent M. Powers; LeeAnn Gorthey

(57) ABSTRACT

Disclosed are an apparatus, system, and method for two dimensional electrophoresis of analytes of interest, particularly polypeptides. The apparatus includes a sample separation cavity comprising (1) an electrophoresis region located along an upper portion of the cavity for performing charge and/or size-based electrophoresis in a first dimension along the upper portion, and (2) below the electrophoresis region, a second electrophoresis region for performing electrophoresis in a second dimension in a direction substantially perpendicular to the first dimension. In one preferred embodiment, the second electrophoresis region contains an isoelectric focusing region containing a continuous pKa gradient immobilized on at least one of the major opposing surfaces of the cavity.

26 Claims, 2 Drawing Sheets

U.S. PATENT DOCUMENTS

| | | | |
|---|---|---|---|
| 5,540,826 | * | 7/1996 | Bier et al. .............................. 204/610 |
| 5,755,943 | | 5/1998 | Middendorf et al. . |
| 5,773,645 | * | 6/1998 | Hochstrasser ....................... 204/456 |
| 5,837,116 | | 11/1998 | Harrington et al. . |
| 5,885,432 | * | 3/1999 | Hooper et al. ....................... 204/469 |
| 6,013,165 | * | 1/2000 | Wiktorowicz et al. .............. 204/456 |

* cited by examiner

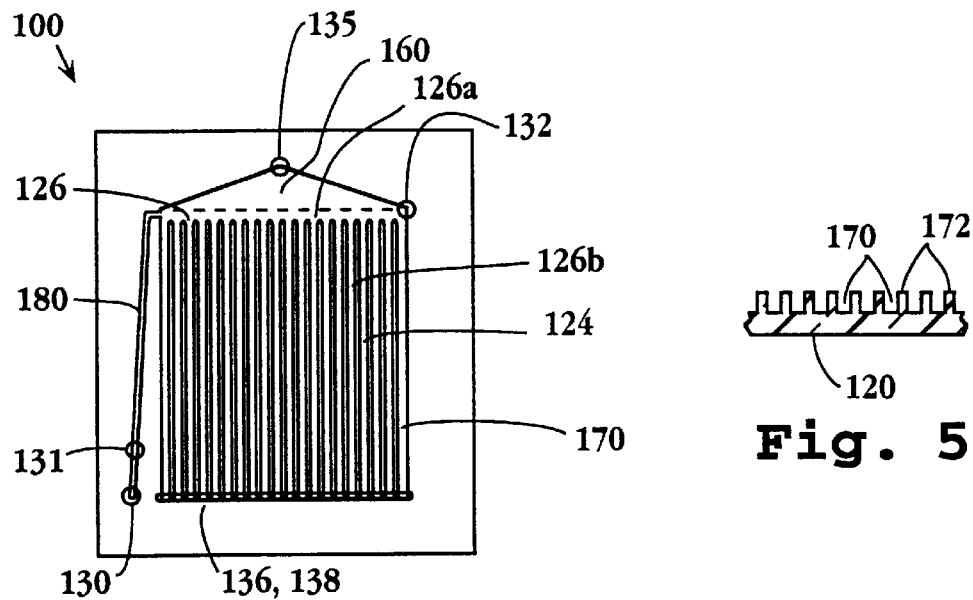
Fig. 3
Fig. 5
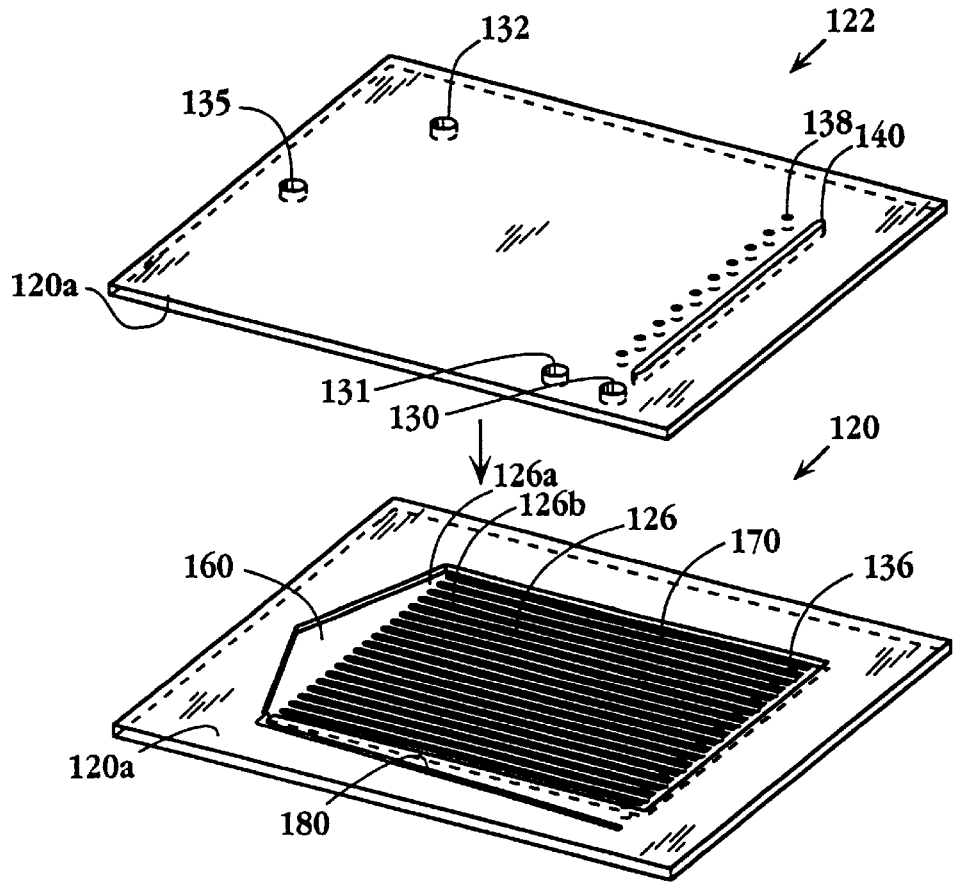
Fig. 4

ELECTROPHORESIS APPARATUS AND METHOD

This application is a continuation of Ser. No. 09/084,041, filed on May 22, 1998, now U.S. Pat. No. 6,013,165 which is hereby incorporated by reference in its entirety.

FIELD OF THE INVENTION

The present invention relates to methods and apparatus for electrophoretically separating and characterizing sample analytes. In particular, the invention relates to multidimensional electrophoresis.

REFERENCES

Alfonso, E. S. et al., *J. Chromatogr.* 689:85–96 (1995).

Anderson, N. L. et al., *Electrophoresis* 12:907–930 (1991).

Andrews in *Electrophoresis. Theory, Techniques and Biochemical and Clinical Applications*, Oxford U. Press, Oxford, p. 276 (1986).

Bjellqvist et al., *Biochem. BioPhys. Meth.* 6:317–339 (1982).

Busch, M. H. A. et al., *J. Chromatogr.* 695:287–296 (1995).

Bushey et al., *J. Chrom.* 480:301 (1989).

Capelli, L. et al., *J. Biochem. BioDhvs. Meth.* 32:109 (1996).

Chen et al., *J. Lig. Chrom.* 15:1143 (1992).

Fung, E. N. et al., *Anal. Chem.* 67:1913–1919 (1995).

Ganzler, K. et al., *Anal. Chem.* 64:2665–2671 (1992).

Gilges, M. et al., *Anal. Chem.* 66:2038–2046 (1994).

Lauch., T. et al., *J. Chromatogr.* 680:375–381 (1994).

Li in *Capillary Electrophoresis. Principles, Practice, and Applications*, Elsevier, Amsterdam, p. 160 (1992).

Liao, J.L. et al., *J. Cap. Elec.* 2:191 (1995).

Molteni, S. et al., *Electrophoresis* 15:22–30 (1994).

Ng, C. L. et al., *J. Chromatogr.* 659:427–434 (1994).

Peterson et al., EP Publ. No. 494686 A1 (1992).

Righetti, P. G., *Immobilized pH Gradients: Theory and Methodology*, Elsevier, Amsterdam (1990).

Righetti, P. G. et al., in *Gel Electrophoresis of Proteins*, B. D. Hames and D. Rickwood, Eds., IRL Press, Oxford, p.149 (1996).

Sandoval and Pesek, U. S. Pat. No. 5,017,540 (1991).

Sandoval and Pesek, U. S. Pat. No. 5,326,738 (1994).

Schans, M. J. et al., J. Chromatogr. 680:511–516 (1994).

Sun, P. et al., *J. Microcol Sep.* 6:403–407 (1994).

Wang, T. et al., *J. Chromatogr.* 594:325–334 (1992).

Werner, W. E. et al., *Anal. Biochem.* 212:253–258 (1993).

Wiktorowicz, J., U.S. Pat. Nos. 5,015,350 (1990) and 5,181,999 (1991).

Wilkens, M. R. et al., Eds., *Proteome Research: New Frontiers in Functional Genomics*, Springer Verlag, Berlin, Germany (1997).

Wong, S. S., *Chemistry of Protein Coniugation and Cross-Linking*, CRC Press, Boca Raton, FL (1991).

Zhu et al., *J. Chrom.* 516:123 (1990).

BACKGROUND OF THE INVENTION

For decades, electrophoretic separation methods have been central to identifying and characterizing chemical and biochemical samples. In the usual procedure, an electrophoresis tube or slab is filled with a fluid electrophoresis medium, and the fluid medium is covalently cross-linked or temperature-solidified to form a non-flowable, stabilized gel separation medium. A sample is loaded into one end of the tube, or into one or more wells of the slab gel, and an electric field is generated to draw the samples through the medium. Electrophoretic separation may depend predominantly on molecular size, e.g., in the cases of nucleic acids and SDS-bathed proteins, or on a combination of size and charge, as in the case of non-denaturing gel electrophoresis of polypeptides or polysaccharides, for example.

Isoelectric focusing (IEF) is an electrophoresis method based on the migration of a molecular species in a pH gradient to its isoelectric point (pI). The pH gradient is established by subjecting an ampholyte solution containing a large number of different-pI species to an electric field, usually in a crosslinked matrix. Analytes added to the equilibrated ampholyte-containing medium will migrate to their isoelectric points along the pH gradient.

For complex samples, multidimensional electrophoresis methods have been employed to better separate species that comigrate when only a single electrophoresis dimension is used. The conventional approach to two dimensional electrophoresis is to perform the first dimension in a rigid, usually crosslinked matrix. For analysis of proteins, for example, the sample is usually fractionated first by IEF in a tube or strip gel to exploit the unique dependence of each protein's net charge on pH. Next, the gel containing the separated proteins is extruded from the tube, dried (these two steps can be bypassed using a strip gel) and laid horizontally along one edge of a slab gel, typically a crosslinked polyacrylamide gel containing sodium dodecylsulfate (SDS). Electrophoresis is then performed in the second dimension, perpendicular to the first, and the proteins separate on the basis of molecular weight. Thus, proteins having similar net charges, and which are not separated well in the first (IEF) dimension, will separate according to their different masses in the second dimension. Since these two separation methods depend on independent properties (net charge and mass), the overall resolution is approximately the product of the resolution in each dimension.

A significant drawback of traditional methods for two-dimensional electrophoresis is that two separate devices are used to accomplish electrophoresis in the two dimensions. These protocols can be very time-consuming and cumbersome to practice. Moreover, traditional methods are susceptible to significant run-to-run variation because of variability in standard IEF and SDS gels, which cannot be re-used.

Accordingly, there is a need for a new multidimensional electrophoresis method that is faster and easier to use, which allows the identification and characterization of hundreds or thousands of components in complex mixtures, and which is highly reproducible. Ideally, the method will employ a single separation apparatus for electrophoresis in both dimensions. The method preferably involves a flowable (liquid-state) separation medium that can be easily replaced with fresh media, so that a single apparatus can be used repetitively for multiple samples. Ideally, the apparatus is adaptable for automation.

SUMMARY OF THE INVENTION

The present invention is directed to methods and apparatus for conducting multidimensional electrophoresis of samples within a single apparatus, such that sample components that have been resolved in a first electrophoretic dimension can be directly electrophoresed in a second dimension that is substantially perpendicular to the first, without needing to move or manipulate the sample between the first and second electrophoretic steps.

In one aspect, the invention includes a two-dimensional electrophoresis system. In one embodiment, the system includes an electrophoresis plate assembly that defines (i) a sample separation cavity, (ii) a sample loading port positioned at a corner of the upper portion, for introducing a sample into the electrophoresis region, and (iii) optionally, one or more fluid passageways positioned along the lower portion of the cavity, for introducing or removing liquid from the cavity.

The cavity defined by the assembly is bounded by opposing major first and second surfaces, each having a defined width and length. These major surfaces are spaced apart by an interfacial distance substantially shorter than the width and length of the cavity. The cavity further comprises (1) a first electrophoresis region located along the upper portion of the cavity for performing charge and/or size-based electrophoresis in a first dimension along said upper portion, and (2) below the first electrophoresis region, a second electrophoresis region for performing electrophoresis in a second dimension in a direction substantially perpendicular to the first dimension, such that the rate of migration of sample components in the second dimension depends on sample properties that are different from the sample properties that determine the rate of migration in the first dimension.

In one embodiment, the second electrophoresis region is an isoelectric focusing region containing a continuous pKa gradient immobilized on at least one of the major opposing surfaces, for isoelectric focusing in a direction substantially perpendicular to the first dimension. The pKa gradient may span any attainable range, such as a pKa range of about 4 to 10, or 4 to 6, for example.

In another embodiment, the second electrophoresis region does not contain a pKa gradient and is used to perform charge and/or size-based electrophoresis under conditions different from the electrophoretic conditions used for the first dimension.

The system may further include electrode means for generating a first voltage potential across the first electrophoresis region between the loading port and the lateral portion across from the loading port, electrode means for generating a second voltage potential between the upper portion and lower portion, and an aqueous medium occupying the cavity.

In one embodiment, the loading port is joined to the upper corner portion of the cavity by an elongate sample transport channel.

In another embodiment, the one or more fluid passageways are provided as a single slot which passes through one of major surfaces near the lower portion. In an alternative configuration, the one or more fluid passageways comprise a plurality of openings positioned along the lower portion of the cavity.

In another embodiment, the second electrophoresis region contains a plurality of elongate separation channels defined by the plate, which are substantially parallel to the lateral portions of the cavity and prevent flow of the medium between adjacent separation channels. The second electrophoresis region preferably contains at least 30 separation channels, and preferably more than 100 separation channels.

In another embodiment, the plates define a fan-shaped region that abuts the upper portion of the separation cavity, for introducing or removing liquid from the cavity.

In another aspect, the invention includes an electrophoresis plate assembly, such as described above.

In another aspect, the invention includes a method for separating one or more components of a sample mixture, using an electrophoresis plate assembly or system such as those described above. In the method, a sample mixture is applied to the sample loading port. A first voltage potential is applied across the first electrophoresis region under conditions effective to cause different components in the mixture to migrate towards the opposite portion of the electrophoresis region, such that different components become separated at least partially on the basis of size. After electrophoresis in this first dimension, a second voltage potential is applied across the upper and lower portions of the cavity, in a direction substantially perpendicular to the first dimension, under conditions effective to separate different components on the basis of charge and/or size features that are different from those used in the first dimension. In one embodiment, the second electrophoresis region is an isoelectric focusing region, and the electrophoretic conditions are effective to generate a pH gradient in the isoelectric focusing region in a direction substantially perpendicular to the direction of the first voltage potential. Sample components migrate into the isoelectric focusing region and separate on the basis of their isoelectric points.

In a second embodiment, the second electrophoresis region does not contain a pKa gradient, and the second electrophoretic conditions are effective to perform charge and/or size-based electrophoresis under conditions different from the electrophoretic conditions used for the first dimension.

After electrophoresis in the second dimension is complete, sample components can be detected and imaged to obtain information about the composition of the sample. To facilitate detection, sample components preferably contain a detectable label, such as a fluorescent label or radiolabel. In a preferred embodiment, the sample comprises one or more polypeptides to be detected.

In one embodiment, after electrophoresis in the second dimension is complete, one or more sample components can be collected from the separation cavity for further characterization. Preferably, the second electrophoresis region includes a plurality of elongate separation channels as above, to facilitate collection of sample components.

These and other features and advantages of the present invention will become more clear from the following detailed description together with the appended drawings.

BRIEF DESCRIPTION OF THE DRAWINGS

FIG. 3 illustrates another exemplary plate assembly in accordance with the invention, which additionally includes a liquid loading region, a plurality of separation channels, and an elongate sample transport channel;

FIG. 4 shows a perspective view of the assembly of FIG. 3; and

FIG. 5 shows a cross-section of the channel region of the assembly from FIGS. 3 and 4.

DETAILED DESCRIPTION OF THE INVENTION

As noted above, the present invention is directed to methods and apparatus for conducting multidimensional electrophoretic separations of sample mixtures within a single separation cavity, such that the separation conditions in the first dimension are different from the separation conditions in the second dimension.

The invention is adaptable to a variety of separation conditions, including conditions for (1) isoelectric focusing, and (2) denaturing or non-denaturing size-based separations in flowable sieving media. Moreover, since electrophoresis can be accomplished in both dimensions with flowable (i.e., liquid) media, the medium can be replenished after each sample separation without having to separate the plates.

I. Apparatus

In one aspect, the invention provides apparatus for conducting two-dimensional electrophoresis of selected analytes, particularly polypeptides. The following discussion is directed to a first embodiment of the invention wherein electrophoresis in the first dimension is performed on the basis of size and charge, and electrophoresis in the second dimension is performed on the basis of isoelectric focusing (IEF). Other, alternative embodiments are discussed subsequently.

Figure 1:
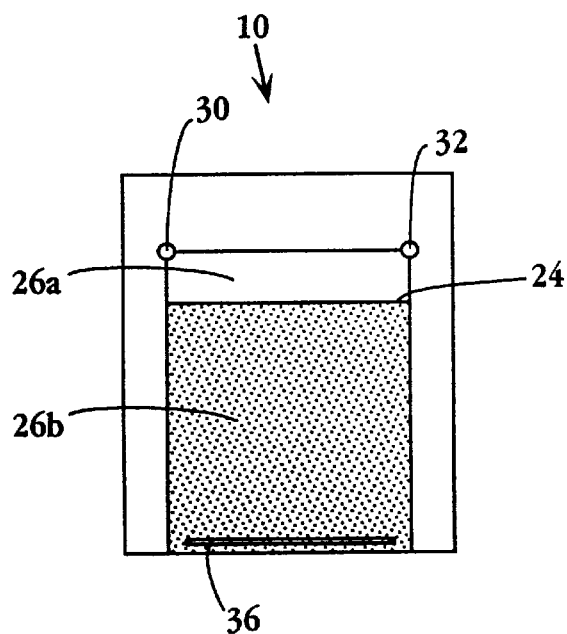
FIG. 1 shows an overhead view of a plate assembly in accordance with the invention.
Figure 2:
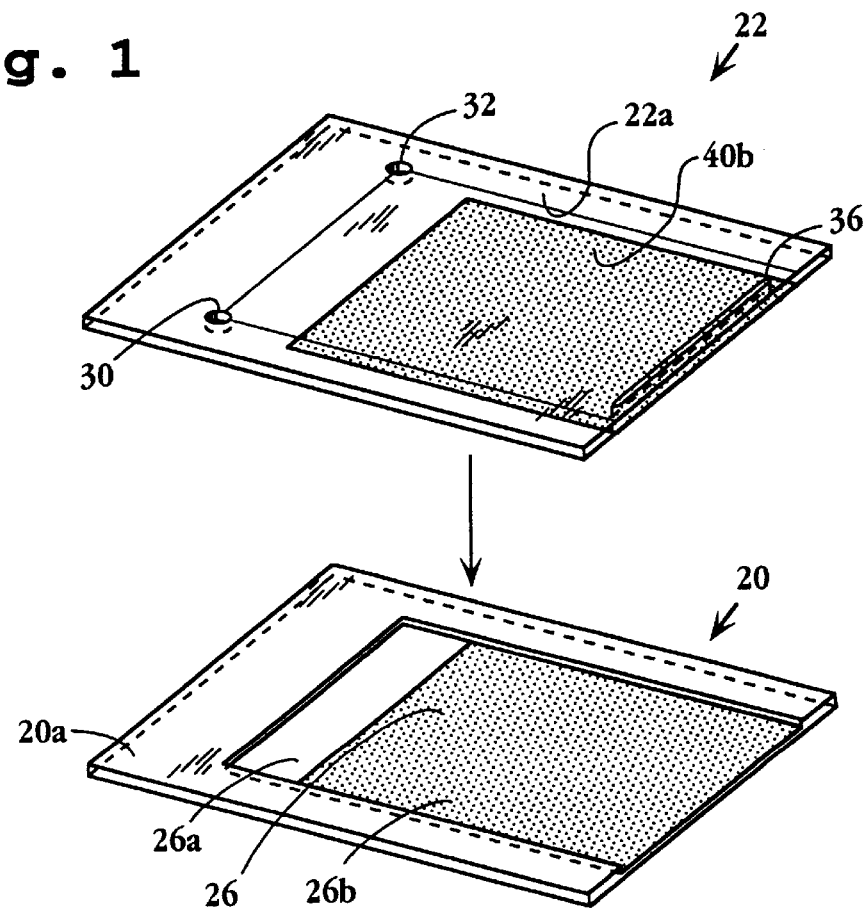
FIG. 2 shows a perspective view of the assembly of FIG. 1.

FIGS. 1 and 2 show an overhead view and perspective view, respectively, of an electrophoresis plate assembly 10 in accordance with the present invention. A pair of plates 20, 22 are disposed such that inner plate surfaces 20a and 22a are juxtaposed face-to face to form an enclosed separation cavity 24, for holding a separation medium through which the sample is electrophoresed.

Plate 20, which is also referred to arbitrarily as the bottom plate, defines a recessed region 26 which defines five of the six walls of cavity 24. As seen with reference to FIG. 2, region 26 further includes a first sample separation surface, designated surface 26a, for electrophoresis along the lateral dimension of this region, and a second sample separation surface 26b, for electrophoresis in a direction perpendicular to the first-mentioned dimension.

For an IEF embodiment of the invention, surface 26b is further characterized by the presence of a plurality of buffering moieties, or Immobilines, which define a continuous pKa gradient leading away from region 26a. The properties of region 26b are discussed further below.

Plate 22, which is also referred to arbitrarily as the cover plate, includes an inner surface 22a which is substantially flat, for providing the sixth wall of separation cavity 24. As seen particularly with reference to FIG. 2, plate 22 defines, in its upper left-hand corner, a sample loading port 30, at or through which sample is introduced into the separation cavity, and which also provides access to the separation cavity for a first electrode 30a (not shown) for establishing a voltage potential at that site. An electrode port 32 is defined in the upper right-hand corner of plate 22, for providing a second electrode 32a (not shown) in electrical contact with the separation cavity.

The apparatus may include an optional third electrode 34a (not shown), which is electrically separate from the first and second electrodes mentioned above, and which extends laterally across the top of cavity 24. This third electrode can be admitted into the separation cavity through port 30 or 32, and can be immobilized in the cavity by being affixed, for example, to the bottom plate along the upper edge of recessed region 26.

Plate 22 also contains an elongate slot 36 which extends laterally along the bottom of the plate, for providing (i) an electrode 36a (not shown) extending along the bottom of the separation cavity, and (ii) a passageway for ingress and egress of separation media and wash solutions into and out of the separation cavity before or after electrophoresis.

Preferably, the surfaces 26a and 26b of recessed region 26, and the inner surface 22a of cover plate 22, are substantially planar, to facilitate the creation of undistorted electric field lines and enhance sample separation during electrophoresis.

The inner surface 22a of the cover plate preferably includes a surface region 40b whose dimensions are congruent with and opposite to surface region 26b in plate 20, for generating an isoelectric focusing pH gradient in the separation medium located in that region. Like region 26b, for isoelectric focusing, region 40b is preferably coated with a plurality of buffering moieties, or Immobilines, which define a continuous pKa gradient leading away from the region 26a.

Plates 20, 22 can be formed of any material suitable for electrophoresis of the selected sample. Preferably, at least one of the plates is formed of a material that is transparent with respect to a type of signal that is used to visualize or locate sample components in the separation cavity. Typically, the plates are formed out of a silicon dioxide-based glass, such as borosilicate, although other materials such as plastics, such as polycarbonate, or metals rendered non-conductive by a suitable coating, are also contemplated. Visually opaque materials such as TEFLON™ and MYLAR™, for example, can also be used, e.g., with radioactive sample detection.

In a preferred embodiment, both plates are made from borosilicate glass. Glass is advantageous because it is transparent to a broad range of wavelengths, e.g., for fluorescence detection and visual inspection, it can be cut easily, and fine features on the order of 1 to 100 $\mu$m or greater can be formed in glass by standard photolithographic etching techniques. For example, a recess region 26 having a substantially planer surface with a depth of 100 $\mu$m can be formed readily by conventional hydrofluoric acid etching. Similarly, ports 30, 32 in cover plate 22 can be formed by mechanical drilling, for example.

In the assembled apparatus (plate assembly), plates 20 and 22 are joined together by any suitable means that are sufficient to ensure a liquid-tight seal with respect to separation cavity 24. For example, glass plates can be fusion-welded together using methods known in the art, i.e., by holding the opposing faces of the plates together at an elevated temperature that is below the softening point of the plates, such that the inner surfaces 20a and 22a of the plates become bonded together. Alternatively, the plates can be joined together by anodic bonding, or simply by using one or more clamps along the edges of the plates.

FIGS. 3 and 4 illustrate another exemplary embodiment of an apparatus (100) of the invention which additionally includes a liquid loading region 160, a plurality of separation channels 170, and an elongate sample transport channel 180.

In this example, bottom plate 120 (FIG. 4) contains a recessed region 126 which defines five of the six walls of separation cavity 124. Region 126 includes a first sample separation surface 126a, for electrophoresis along the lateral dimension of this region, and a second sample separation surface 126b for isoelectric focusing. Edge region 120a surrounds region 126.

Region 126 also encompasses a fan-shaped liquid loading region 160 at the upper end of the plate, for conveniently introducing and removing separation media to and from the separation cavity before and after electrophoresis. Region 160 is also useful for forming a pKa gradient coating on the inner surfaces of the plates for isoelectric focusing, as detailed below.

With continued reference to FIGS. 3 and 4, surface 126b comprises a plurality of parallel separation channels 170 that are aligned in a direction perpendicular to the bottom edge of the plate. For an IEF embodiment of the invention, the channels are each coated with a plurality of buffering moieties, forming a continuous pKa gradient in the vertical direction with respect to the top and bottom edges of the plates. Each channel 170 is separated by a partition 172 (FIG. 5) having a height that is flush with inner surface 120a of plate 120. This is preferred in order to form liquid-tight seals between the channels when plates 120 and 122 are assembled together. The depths of the channels are preferably the same, and are also preferably the same as the depths of regions/surfaces 126a and 160.

The number of channels 170, and their dimensions, will vary depending on sample complexity and the desired resolution.

Generally, sample resolution will increase as the number of channels is increased, subject to the limit of resolution achieved by electrophoresis in the first, lateral, dimension. Preferably, the channels are dimensioned so that the channel resolution is at least twice the sample resolution in the lateral dimension of the separation medium, so that each sample band partitions into from one to three channels.

Plate 120 also contains an elongate sample transport channel 180 extending from the lower left hand area of the plate to the upper left hand corner of surface 126a, for size-based electrophoretic separation of the sample during transit to separation cavity 124.

Channel 180 preferably has a depth in plate 120 equal to the depth of recess 126. The width of channel 180 is preferably no more than about 10 times the channels depth, and is preferably equal to or less than about 5 times the channel depth.

Plate 122, which is also referred to arbitrarily as the cover plate, includes an inner surface 122a which is substantially flat, for providing the sixth wall of separation cavity 124. As seen in FIG. 3, and particularly with reference to FIG. 4, plate 122 defines, in its lower left-hand corner, a sample loading port 130, at or through which sample is introduced into the separation cavity, and which also provides access to the separation cavity for a first electrode 130a (not shown) for establishing a voltage potential at that site. An electrode port 132 is defined in the upper right-hand corner of plate 122, for providing a second electrode 132a (not shown) in electrical contact with the separation cavity. The first and second electrodes are useful for performing electrophoresis of the sample along a first dimension stretching from port 130 to port 132, to generate a series of separated sample components along the upper edge of 126a after the first electrophoresis step is complete. Plate 122 also contains an elongate slot 140 which extends laterally along the bottom of the plate, like slot 36 mentioned above.

Port 135 in plate 122 is included for transporting separation media and wash fluids into and out of the separation cavity, and also for forming the IEF coating gradient.

To facilitate sample loading, port 130 can be accompanied by a waste port 131 defined in plate 122, such that both ports are in fluid communication with elongate sample transport channel 180. This allows a precise amount of sample to be injected into channel 180, as discussed further below.

Returning to FIG. 4, plates 120 and 122 further define channel egress ports 136 and 138, which are located slightly above slot 140, for collecting resolved sample components individually from one or more channels after the IEF step is complete. In the embodiment illustrated in the Figure, each plate contains an egress port for alternating channels, so that ports 136 and 138 are staggered relative to each other. The staggering of egress ports, while not required, facilitates the connection of capillary tubes to the ports for collecting fluids from each channel.

The dimensions of the apparatus and assembly are a matter of design choice and are selected for convenience of use. For example, the separation cavity preferably has a length dimension of about 1 to 20 cm (e.g., 12 cm); a width dimension of about 1 to 50 cm (e.g., 10 cm); and a depth dimension (interfacial distance between the major opposing surfaces of plates) of about 50 to 200 μm (e.g., 100 μm); the first electrophoresis region preferably has a path width of about 0.1 to 2 cm (e.g., 0.25 cm); channels 170 preferably have a widths of about 0.25 to 1 mm (e.g., 0.67 mm), depths that are preferably the same as the above-mentioned interfacial distance, and are spaced apart by partitions having a width of about 0.1 to 0.5 mm (e.g., 0.33 mm); elongate channel 180 preferably has a length of about 0.5 to 15 cm (e.g., 12 cm), a width of about 0.2 to 1 mm (e.g., 0.5 mm), and a depth that is preferably the same as the above mentioned interfacial distance); slot 140 preferably has a length spanning all channels, and a width of about 0.5 to 3 mm (e.g., 2 cm); ports 130, 131, 132, 135 and 136/138 preferably have diameters of 0.5 to 3 mm (e.g., 1 mm); and ports 130 and 131 are spaced apart by a center-to-center distance of 0.5 to 2.5 cm (e.g., 1.2 cm). Of course, dimensions outside the above preferred dimensions can also be used.

With reference to the embodiments illustrated in FIGS. 1 to 5, the inner surfaces of the separation cavity are preferably inert with respect to the sample, to minimize adsorption of the sample to the inner surfaces during electrophoresis. Such adsorption is generally undesirable because it can disrupt band resolution particularly in the first dimension of electrophoresis. Additionally, materials such as silicate glasses tend to have charged groups on their surfaces that can cause electroendosmotic flow (EOF) of the separation medium during electrophoresis. EOF is a phenomenon in which a bulk flow of the electrophoresis medium arises due to the effect of the electric field on counterions adjacent to charged surfaces of a separation cavity. In the case of a surface that is negatively charged, such as a silicate glass surface, there is a build-up of positive counterions (cations) in the solution adjacent to the surface. In an electric field, this shell of cations can cause the medium to migrate toward the cathodic electrode at an EOF rate dependent on the thickness of the cationic shell.

The rate of EOF can provide an important variable that can be optimized to improve the separation of two or more closely migrating species. In particular, when electrophoresis is carried out under conditions in which EOF and the migration of species to be separated are in opposite directions, the effective path length for separation can be made extremely long by making the rate of EOF in one direction nearly equal to the electrophoretic migration rate of the analyte attracted most strongly in the opposite direction by the electric field. In the present invention, EOF may or may not be desirable for the first dimension of electrophoresis, depending on the nature of the sample and the degree of desired separation. However, for the second (IEF) dimension of electrophoresis, EOF is preferably avoided so that the uniformity of the IEF pH gradient is not disturbed.

If the materials from which the plates are made are not inherently sufficiently inert towards the sample, the inner surfaces of the plates and all other inner surfaces of the separation cavity can be coated with any suitable coating material, to reduce sample adsorption to an acceptable level. Since electrophoresis is usually performed in an aqueous separation medium, adsorption of sample can usually be reduced by covering the inner surfaces of the separation cavity with a hydrophilic coating that masks potentially adsorptive surface regions.

Exemplary reagents for coating adsorptive surfaces include polyacrylamide, polyvinyl alcohol, polyethers, cellulose acetate, polyalkylene oxides, poly(vinylpyrrolidone), and other materials as are known in the art. Preferably, such coatings are attached to interior surfaces covalently, although coating by adsorption may also be suitable.

Coating reagents for reducing sample adsorption can also be used to control the magnitude of EOF. For example, EOF along glass silicate surfaces can be substantially reduced by coating them with a neutral reagent that masks a substantial percentage of surface silanol groups. The magnitude of EOF can be further controlled by using coating reagents that include positively or negatively charged groups. Positively charged coatings can be used to nullify surface negative charges to give a net surface charge of zero, so that EOF=0. Coatings with higher positive charge densities can be used to reverse the direction of EOF for charged surface materials. This can be useful for slowing the net migration rates of positively charged sample species. Conversely, negatively charged coatings can be used to impart to or increase the magnitude of negative charge on surfaces, to slow the net migration rates of negatively charged species. Representative positively charged coatings include polyethyleneimine, quaternized polyethyleneimine, and chitosans, for example. Representative negatively charged coatings include carboxylate and sulfonate containing materials, such as poly(methyl-glutamate) and 2-acrylamido-2-methylpropanesulfonate polymers, for example. It will be recognized that charged coatings can also effectively reduce sample adsorption, especially for samples having the same charge polarity as the coating.

Sample adsorption and EOF can also be adjusted by including suitable reagents in the separation medium and running buffers. For example, negative surface charges can be masked by including a cationic additive in the medium, such as metal amine complexes, amines and polyamines such as propylamine, triethylamine, tripropylamine, triethanolamine, putrescine, spermine, 1,3-diaminopropane, morpholine, and the like. Zwitterionic species comprising both negatively and positively charged groups that are isoelectric at the pH of electrophoresis can also be used, such as trialkylammonium propyl sulfonates, where alkyl is methyl, ethyl, propyl, etc. (Peterson et al., 1992, Zhu et al., 1990, Bushey et al., 1989, and Chen et al., 1992).

The choice of additives in the separation medium will depend in part on the sample and the nature of the interior surfaces, as well as other factors. In some applications, it may be desirable to use both a covalent surface coating and soluble buffer agents to control sample adsorption and EOF.

According to a preferred embodiment, the second electrophoresis region includes an isoelectric focusing region that contains a continuous pKa gradient immobilized on at least one of the major opposing surfaces, for isoelectric focusing in a direction substantially perpendicular to the first dimension. The pKa gradient is effective to produce an isoelectric focusing pH gradient when the apparatus is filled with an aqueous medium, to promote migration of sample components to locations in the gradient where the local pH is equal to the pI of each component.

The immobilized pKa gradient is formed on one or both major inner surfaces by any method suitable for forming a gradient having a desired pKa range, resolution, and buffering capacity. Generally, forming the pKa gradient entails exposing plates to a solution containing a gradient of Immobilines under conditions effective to promote covalent attachment of the Immobilines to the plates such that the pKa gradient of the solution is transferred to the plates.

In one approach, the immobilized pKa gradient is formed by pumping a solution containing a gradient of Immobiline molecules into the bottom of a vertically oriented separation cavity. The gradient can be formed using a simple binary gradient-forming assembly consisting of first reservoir and second reservoirs connected to a pump. The first reservoir contains a first solution containing low pKa Immobilines, and the second reservoir contains a second solution containing high pKa Immobilines. Initially, the gradient solution is drawn only from reservoir A. As filling progresses, the pump draws an increasing amount of solution from reservoir B instead of A. Although a linear gradient is preferred in most situations, it will be appreciated that curved gradients can also be formed, depending on the design chosen by the user. Also, while a mechanical pump may be most convenient for loading the gradient, other methods such as gravity-based loading can also be used.

The solution in the second reservoir preferably has a mass density greater than that of the solution in the first reservoir, to help maintain the resolution and continuity of the gradient during the loading and attachment of the Immobilines to the IEF region. This is accomplished, for example, by including glycerol or a mono-or disaccharide such as glucose in the second solution.

The sample capacity of the isoelectric focusing region will depend in part on the buffering capacity of the immobilized buffering groups on the major inner surface(s) of the plates. Buffering capacity generally increases as the density of buffering groups on the surface is increased. Thus, it is preferable to attach as high a density of buffer groups to the surface as possible, to allow the plates to accommodate higher concentrations of sample components to be separated on the basis of pI.

The buffering groups for creating the IEF gradient are attached to the plates by any suitable method known in the art. In particular, suitable compounds will include (i) buffering groups having desired pKa values and (ii) reactive groups for covalently binding to chemically complementary reactive groups on the inner surface of the isoelectric focusing region.

A large number of buffering compounds have been developed over the past several decades for creating IEF gradients. Exemplary descriptions of such buffering compounds can be found in Righetti (1990), Bjellqvist et al. (1982), Andrews (1986), and Righetti et al. (1996). The buffering compounds may be coupled directly to the IEF regions of the plates using suitably activated plates or buffering compounds, or may be attached via a crosslinking reagent (e.g., see crosslinking groups reviewed by Wong, 1991). Also, a variety of buffering compounds suitable for covalent attachment to solid phase surfaces are commercially available (e.g., the "IMMOBILINE" compounds sold by Amersham-Pharmacia Biotech, Uppsala, Sweden).

For silicate glass plates, buffering compounds can be attached directly to surface silanol groups, as reviewed in Li (1992) or can be attached via an intermediary coating that provides other reactive groups. A variety of intermediary coating compounds have been described in the literature, such as "bind silane" (3-(trimethoxysilyl)propyl methacrylate, Sigma Chemical Co., St. Louis, Mo.; Capelli et al., 1996), a-glycidoxypropyl trimethoxy silane (Liao et al., 1995), chlorination followed by Grignard or organolithium reaction (Sandoval and Pesek, 1994), and allyl attachment via silane-hydride chemistry (Sandoval and Pesek, 1991, 1994). Immobilization methods that produce Si-C bonds of attachment are generally preferred, to enhance longevity of covalent attachment of the buffering groups to the surface.

Conveniently, IEF buffering groups are attached to the IEF surface region using the two-step silane-hydride chemistry taught by Sandoval and Pesek (1991, 1994). In the first step, a solution of $(EtO)_3SiH$ is washed slowly over the plate surface to deposit Si-H groups (silyl hydrides) over existing silanol groups. It is usually necessary to maintain a constant flow rate of the hydride reagent over the plates to prevent formation of solid deposits inside the separation cavity. Next, the hydride groups are reacted with a dialkene such as allyl methacrylate in the presence of a hexachloroplatinic acid catalyst to bind allyl groups to the surface via a stable Si-C bond. Preferably, this 2-step coating procedure is performed on the entire separation cavity, to coat all free silanol groups. Also, the allyl methacrylate reaction can be repeated to increase overall yield. Exemplary reaction conditions are provided in Example 1.

After the surface silanol groups have been converted to surface allyl groups, the IEF region is contacted with a selected pKa gradient solution. The orientation of the IEF gradient is selected in accordance with (i) the nature of the analytes being separated, and (ii) the expected pH for electrophoresis in the first dimension. If the pH of the electrophoresis medium in the first dimension is acidic (e.g., pH 2), the IEF gradient is usually oriented such that the more acidic pKa buffering groups are proximal to the first separation region, and the more basic pKa buffering groups are distal to the first separation region. Conversely, if the pH of the first dimension will be relatively basic (e.g., pH 10), the orientation of the IEF gradient is reversed, such that the more basic pKa buffering groups are proximal to the first separation region.

To attach the pKa buffering groups to the IEF region, the plate assembly can be positioned vertically (upright) such that the IEF region of the separation cavity is at the bottom for an assembly as shown in FIGS. 1 and 2. If an assembly having an upper fan-shaped loading region 160 is used, such as shown in FIGS. 3 and 4, the assembly is inverted so that region 160 is at the bottom. After the pKa buffer compounds are activated (if necessary), e.g., with a radical-initiator reagent such as TEMED plus ammonium persulfate (APS), the gradient is loaded into the IEF region from below until the IEF region is filled. Preferably, glycerol is included in the second buffer reservoir to minimize mixing of the buffering compounds during loading and immobilization. Also, after the gradient solution has been loaded, the gradient solution can be "chased" with a high-density liquid containing a visible dye, such as bromphenol blue, to ensure that the end of the gradient solution reaches the IEF region. The assembly is then allowed to incubate at a suitable temperature until the pKa buffering compounds become bound to the surface-attached allyl groups. After attachment of the buffering compounds is complete, the reaction mixture can be replaced with water.

In a separate step, which can be carried out before or after the pKa buffering compounds are attached to the IEF region, the surface-attached allyl groups in the first separation region can be reacted with an inert coating material to reduce sample adsorption in this region. Preferably, the allyl groups are reacted with a hydrophilic material, such as linear polyacrylamide, to impart hydrophilicity to the inner surfaces in this region. For embodiments that do not require an IEF gradient region, the inner surfaces of the cavity can be coated with a suitable coating as discussed above, to control EOF and reduce sample adsorption. The separation cavity can then be stored, preferably in water or another suitable fluid, until use.

II. Method and System

In another aspect, the invention includes a method for separating one or more components of a sample mixture, using an electrophoresis plate assembly or apparatus such as described above. The method is useful for identifying and characterizing a variety of samples, and for monitoring changes in sample composition over time.

The sample can be any substance for which electrophoretic separation by the present invention may be useful. Preferred sample-types include polypeptides, glycopolypeptides, proteoglycans, charged polysaccharides, and synthetic polymers, for example, although other substances, especially from biological sources, are also contemplated. Also, the sample may be derived from cellular or tissue extracts (e.g., Anderson et al., 1991), or biological fluids, such as blood, urine, semen, synovial fluid, saliva, or fractions thereof, prepared by known methods.

If necessary, the sample components can be modified to include one or more detectable labels to facilitate detection and quantification in the separation medium. In one approach, the sample is labeled with a fluorescent label, such as a fluorescein, rhodamine, eosin, or "BODIPY™" group, according to methods well known in the art. The reactive functionality on the label is selected to ensure labeling of most or all of the components of interest in the sample. Preferably, the label contains a reactive functionality that reacts with a limited set of complementary reactive groups. For proteins, for example, cysteine-selective reagents are preferred, such as iodoacetamide and maleimide functionalities, since most proteins ($\geq$90–95%) contain at least one. Tyrosine and amine-reactive labels can also be used. Generally, hydrophilic labels are preferred, to help avoid sample precipitation. Fluorescent compounds suitable for labeling proteins and the like are well known, and are commercially available from Sigma Chemical Co. (St. Louis, Mo.) and Molecular Probes, Inc. (Eugene, OR). Preferred derivatized labels include functionalized eosin or "BODIPY", and monobromobimane.

It will be appreciated that although fluorescent derivatization of sample components may alter the pI values of some components, such alterations are acceptable since they do not interfere with detecting and monitoring the components.

A chemical labeling reaction is carried out for a time sufficient to label uniformly most or all labelable components in the sample. Unbound label can be removed by quenching with an excess amount of a scavenger substrate, such as free cysteine, followed by passing the reaction mixture through a size-exclusion gel, such as Sephadex™ G-25 or G-50 (Amersham-Pharmacia Biotech).

Alternatively, the sample may include a detectable radioisotope, such as $^{125}I$, $^{32}P$, $^{35}S$, $^{14}C$, or $^{3}H$. Chemical and biochemical methods for introducing such isotopes into samples are well known in the art.

In operation, a plate assembly having the desired dimensions is selected which contains a continuous pKa gradient in the isoelectric focusing region spanning a desired pI range. For example, for analysis of proteins in a pI range of 4 to 9, the isoelectric focusing region contains a continuous buffer gradient spanning a pKa range of less than or equal to 4 to greater than or equal to 9. The assembly is encased in a device that includes valved inlet/outlet ports and electrodes which form liquid-tight connections with corresponding ports and slot(s) in the cover plate.

Prior to sample loading and separation, the separation cavity of the system is filled with one or more flowable separation media. In a preferred embodiment, the separation medium consists of two solutions, one for each separation region.

For embodiments that utilize IEF in the second dimension, the medium in the second electrophoresis region preferably has a low ionic strength, in order not to interfere with the IEF step. Also, for embodiments in which the first dimension of electrophoresis is performed at an acidic pH, the pH of the medium is typically more acidic than the lowest pKa of the IEF region. This ensures that sample components that have pI values within the pH range of the IEF gradient will migrate into that region during the IEF step. Exemplary acidic buffers for the first dimension of electrophoresis include citrate, formate, and acetate, typically at a concentration of about 1 to 50 mM, and preferably about 5 to 20 mM.

To reduce precipitation of sample components during electrophoresis, and particularly during isoelectric focusing, the separation medium may additionally include one or more neutrally charged denaturing agents or detergents to reduce non-covalent interactions between sample molecules and wall interactions. Exemplary denaturing agents include urea, thiourea, and dimethylformamide (DMF). Exemplary neutral detergents include polyoxyethylene ethers ("tritons"), such as nonaethylene glycol octylcyclohexyl ether ("TRITON" X-100), polyglycol ethers, particularly polyalkylene alkyl phenyl ethers, such as nonaethylene glycol octylphenyl ether ("NONIDET" P-40 or NP-40), polyoxyethylene sorbitan esters, such as polyoxyethylene sorbitan monolaurate ("TWEEN"-20), polyoxyethylene ethers, such as polyoxyethylene lauryl ether ($C_{12}E_{23}$) ("BRIJ"-35), polyoxyethylene esters, such as 21 stearyl ether ($C_{18}E_{23}$) ("BRIJ" 721), N,N-bis[3-gluconamidopropyl]cholamide ("BIGCHAP"), decanoyl-N-methylglucamide, glucosides such as octylglucoside, and the like. The optimal concentration of a denaturing agent or detergent will depend on the particular detergent used. Urea is typically used at a concentration up to about 10 M, for example, with a concentration of 4 M to 8 M being preferred. Generally, the detergent concentration will range from 0.01% to 5% (v:v), and more typically between 0.025 and 2%, although these ranges are not limiting.

The separation medium may also include soluble agents for dynamically coating the walls of the separation cavity, to help reduce endosmotic flow during electrophoresis. Such soluble coating agents include quaternary ammonium-containing polymers (Wiktorowicz (1990, 1991), methyl cellulose derivatives (Molteni et al., 1994), cellulose acetate (Busch et al., 1995), polyethylene oxide (Fung et al., 1995), chitosan (Sun et al., 1994), polyvinyl alcohol (Gilges et al., 1994), polyethylene glycol (Wang et al., 1992), polyethylenimine (Ibid.), and polyethylene oxide-polypropylene oxide-polyethylene oxide triblock copolymers (Ng et al., 1994), for example. Typically, soluble coating agents can be included at concentrations of about 0.05% to about 4%, and more preferably of about 1% to about 2%.

In a particularly preferred embodiment, the separation medium contains a polymer material (also referred to as "entangled polymer") that differentially impedes sample components on the basis of their sizes. A variety of polymer materials that promote size-based separation of analytes are known in the art, such as linear polyacrylamide (Werner et al., 1993), polyethylene oxide (Schans et al., 1994), dextran (Lauch et al., 1993), polyethylene glycol (Ganzler et al., 1992), and polyvinyl alcohol (Alfonso et al., 1995). The appropriate concentration and size of the polymer material included in the medium will generally depend at least in part on the physical properties and complexity of the sample being analyzed, the properties of the selected polymer(s), and the desired range of component molecular weights to be resolved. For example, if only components with a high molecular weight are of interest, a higher concentration of polymer is used, which allows low molecular weight components to pass through quickly while larger components migrate more slowly. Preferably, the separation medium remains flowable, that is, substantially in liquid form, so that the medium can be easily removed from or replaced in the apparatus by moderate pressure differentials (e.g., less than 50 psi). Further guidance regarding the choice of polymer material, size and concentration can be found in the references cited above. In a preferred embodiment, the polymer material is linear polyacrylamide, e.g., 3% w/v with an average molecular weight (MW) of 100–300 kDa.

The inclusion of such polymer materials is useful for enhancing the level of sample separation in the first dimension of electrophoresis, wherein sample components can be separated on the basis of a combination of their sizes and net charges. Such polymer materials may also be useful for reducing convection currents in the separation medium during and after electrophoresis. A further advantage is that these polymers do not interfere with the isoelectric focusing step.

The invention will now be further illustrated with respect to an embodiment wherein electrophoresis in the first dimension is based on charge and size of the sample components, and electrophoresis in the second dimension is based on pI (by IEF). With reference to the assembly illustrated in FIGS. 3 and 4, a low-ionic strength solution, preferably containing one or more denaturing reagents such as urea and thiourea, is loaded into the separation cavity via ports 130 and 135, with egress through elongate slot 138 until residual air bubbles have been removed from the cavity. Slot 138 is then closed, and valves at ports 135, 130 and 132 are opened to admit a second electrophoresis solution via port 135 into regions 160 and 126a and elongate channel 180. This second solution is preferably a low pH, flowable entangled polymer solution as above, for effecting size-based separation in the first dimension. Some diffusion between the two solutions in the cavity may occur, but this should not significantly affect performance.

For electrophoresis, the plate assembly is preferably oriented horizontally, to minimize convection currents in separation medium. To control temperature, the plates can be placed on a constant-temperature heating/cooling device, such as a Peltier device, to maintain the separation medium at a selected temperature (e.g, 0 to 40°) and prevent overheating. The device preferably includes an elongate sample transport channel 180, as shown in FIGS. 3 and 4, to lengthen the migration distance in the first dimension, and to increase spacing between bands.

With the plate equilibrated with the appropriate solutions, sample injection can be accomplished by hydrodynamic or electrophoretic means. Referring to the embodiment in FIGS. 3 and 4 for illustrative purposes, hydrodynamic injection is performed by closing all ports and slot(s) except ports 130 and 131, and pumping a selected volume of sample through the injection chamber (i.e., the portion of channel 180 located between ports 130 and 131). The sample can be moved into the portion of channel 180 beyond port 131 by closing port 131, opening port 132, and pumping the appropriate volume of buffer solution through port 130. The injection chamber can then be purged of residual sample by closing port 132 and opening port 131 again, to wash a selected amount of solution through the injection chamber. Electrophoretic sample injection can be accomplished by filling the injection chamber with a selected amount of sample via ports 130 and 131 as above, closing those ports, and then applying an electric field between ports 130 and 132 for a selected time (e.g., 5 kV for 1 to 5 seconds) so that a small aliquot of positively charged sample (components with pI values greater than the pH of the medium) migrates into the separation channel upstream of port 131. Note that sample migration can be monitored, for example, by illumination with UV light, for fluorescent samples.

The advantages of hydrodynamic over electrophoretic injection schemes are well-known and are mainly concerned with the oversampling of faster migrating components in electrophoretic injection. Hydrodynamic injection does not suffer from this shortcoming since all components are injected within the solution. Higher sensitivity may be experienced with electrophoretic injection, however, since only sample molecules (not buffer or water) enter the separation path, and sample components are more highly concentrated at the start. However, sensitivity can be improved for hydrodynamic injection by using a sample buffer that has lower ionic strength than the buffer solution in channel 180, to promote sample stacking. The amount of sample injected for analysis will vary according to the complexity of the sample, the type of detection, etc. By way of illustration, a sample volume may consist of 40 nL of a 100 μg/mL sample mixture of 1,000–10,000 fluorescently labeled polypeptides.

After sample loading is complete, electrophoresis is performed across region 126a (first dimension) by applying an electric field between ports 130 and 132 (e.g., 5 to 30 kV), so that injected sample components migrate through channel 180 and into region 126a towards a cathodic electrode at port 132. This process may be monitored in real-time, e.g., by illumination with UV light. A constant field or pulsed field can be used, depending on the sample and the desired resolution. When the fastest migrating component reaches port 132, the field is turned off, and a new field is applied across region 126 in a direction substantially perpendicular to the first dimension. This field can be generated by balancing the electric potentials at ports 130 and 132 to establish a substantially uniform field vertically across regions 126a and 126b towards slot 140. In another approach, this field is generated using an elongate wire electrode which (i) is electrically isolated from point electrodes located at ports 130 and 132, (ii) enters region 126a via port 132, and (iii) spans the upper edge of region 126a. In a third approach, the field is generated using electrodes located at port 135 and slot 140.

The first dimension of electrophoresis is usually completed within a few minutes, depending on the magnitude of the field. For example, cationic polypeptides can migrate approximately 20 cm within 10 minutes in a field of 250 V/cm. Longer electrophoresis times in the first dimension, or lower concentrations of entangled polymers, can be used to select for slower-migrating components. Focusing in the second dimension is typically complete in less than 10 minutes in a field of 500 V/cm (5 kV field over 10 cm). Two-dimensional separations can thus be performed well within one hour, usually within 15 minutes.

The maximum field permissible is dependent on the ability of the device to dissipate Joule heat, which is typically accomplished by contact-cooling (e.g., using a Peltier device) or by convective cooling (e.g., high Reynolds number air-flow).

Other two-dimensional embodiments encompassed by the invention include the following first-dimension/second-dimension combinations:

(1) Non-SDS Denaturing/Non-SDS Denaturing. In this embodiment, the separation cavity contains different media in the first and second electrophoresis regions such that the basis of sample migration in the second dimension is different from that of the first dimension (i.e., sample migration in the second dimension depends on sample features different from those in the first dimension). For example, the first separation region can contain a medium with an acidic pH (e.g., 2.5) and a low concentration of sieving components (e.g., 2% linear acrylamide), and the second region can contain a medium with a more basic pH (e.g., 8) and a higher concentration of sieving components (e.g., 4% linear acrylamide). (2) IEF/SDS-Electrophoresis. In this embodiment, the first electrophoresis region contains an immobilized pKa gradient within region 26a, with an appropriate low-ionic strength buffer, the second electrophoresis region contains an SDS-containing buffer (but not a pKa gradient), and plate 122 additionally contains a lateral slot 190 (not shown) in loading region 160, just above region 26a, which is similar in dimensions to lateral slot 140. After electrophoresis in the first dimension, an SDS-containing buffer is loaded into region 160 via port 135, with egress through slot 190. An electric field is then applied between slot 190 and slot 140 so that SDS molecules diffuse into region 26a. The SDS molecules associate with, and impart negative charge to, the neutrally charged sample components in region 26a, so that the components are drawn into region 26b for size-based separation.

It will be appreciated that the invention can be adapted to other combinations of separation modes, according to the needs of the user.

After electrophoresis has been performed for a selected time, separated bands can be detected, localized, and/or quantified in a variety of ways, including photography, confocal fluorescence scanning, phosphor imaging plates (for radioactivity detection), and by CCD (charge-coupled detection), depending on the nature of the signal being detected. According to one advantage of the invention, signal acquisition can be performed while the electric field is maintained across the IEF region, so that samples can be integrated over time. The components are preferably indexed and recorded using an automated recording device, such as a computer-controlled digital imaging device (e.g., CCD) linked to a low-power microscope. Optical absorbance densitometry techniques can also be used.

If both plates are optically transparent, transmission-type signal detection can be used, as in the case of fluorescence detection involving excitation or illumination from beneath, and detection above, the plates. Alternatively, signal generation (if necessary) and detection can take place above a single plate surface, e.g., for confocal fluorescence detection or radiolabel detection.

For embodiments involving separation channels in the second electrophoresis region, selected sample lanes can be collected through one or more egress ports. For each selected channel, a small-diameter capillary tube is inserted into the egress port, and fluid is withdrawn through the capillary by positive pressure, vacuum, piezoelectric pumping, or electroosmotic pumping. A diode detector can be used at the end of the capillary tube to monitor sample bands entering the tube. The withdrawn sample can be transferred to collection vials or membrane if desired. For configurations having channels that terminate with open ends at the lower ends of the plates, samples may be collected on a membrane by dragging the membrane across the ends of the plate assembly, or by attaching tubes to the channel termini to withdraw sample.

III. Utility

The present invention provides methods and apparatus for characterizing, detecting and/or identifying hundreds or thousands of components in a sample on the basis of different charge and mass properties. The invention therefore has utility in a number of applications, including "fingerprinting" samples, e.g., for differential display to facilitate identification and differentiation of samples; detecting and/or monitoring compositions of normal and diseased cells and tissues; diagnosing or monitoring disease; characterizing or monitoring molecular expression levels of gene products; characterizing the effects of the addition, mutation, deletion or truncation of genes; detecting, identifying, distinguishing, or otherwise characterizing viruses, bacteria, fungi, and other microbes, or components or products thereof; monitoring analyte levels over time as a function of environmental change, life cycle, or exposure to exogenous chemicals or stimuli; toxicity testing; and testing drug candidates for therapeutic efficacy. The method is particularly of interest in studying and characterizing protein components of biological samples, and therefore is useful in proteome research (Wilkens et al., 1997).

From the foregoing, it can be seen how the objectives and features of the invention are met. The invention provides a method that permits two-dimensional electrophoresis in a single apparatus.

The apparatus is simple to use and can generate analytical results more rapidly than previous two-dimensional methods. The method permits characterization of samples containing hundreds or thousands of components under a variety of different separation conditions. The method does not require a crosslinked matrix, and therefore is easily refilled with the same or different media for separating additional samples. By using a chemically stable pKa gradient that is immobilized on one or more interior surfaces of the separation cavity, the apparatus can be reused with high reproducibility, especially with respect to the IEF dimension. Thus, there is no need to form a new pKa gradient for each sample. Furthermore, the use of separation channels in the second dimension facilitates collecting selected lanes or individual analytes for further characterization, after the pattern of analytes has been imaged and indexed.

The invention can be further understood in light of the following examples, which are not intended to limit the scope of the invention.

Materials and Methods

All solvents were obtained in the highest purity available and then passed through a 0.22 $\mu$m filter. Triethoxysilane (TES, Huls America, Bristol, PA), hydrogen hexachloroplatinate IV (Aldrich Chemical), and allyl methacrylate (Aldrich Chemical) were used as received from the manufacturer. Immobilines (pKa=3.6, 4.6, 6.2, 7.0, 8.5 and 9.3) and TEMED were used as received from the manufacturer (Amersham-Pharmacia Biotech). Water was purified with a Milli-Q System and filtered through a 0.45 $\mu$m filter.

EXAMPLE 1

Isoelectric Focusing Region

A plate assembly made from etched borosilicate glass having a configuration substantially in accordance with FIGS. 1 and 2 was used, with a separation cavity having dimensions of 10 cm×10 cm×100 $\mu$m. Prior to derivatization with Immobilines, the channel region was preconditioned at room temperature by treatment a ≈6 mM ammonia solution, pH 10. After rinsing with deionized water and flushing with 0.1 M HCl to remove adsorbed ammonia, the channels were rinsed with deionized water, and the separation cavity was dried with nitrogen at 100° C. for 20 hours or more.

Attachment of Immobilines was accomplished as follows. First, allyl methacrylate moieties were attached to the entire separation cavity in a two-step process described below. Both steps were conducted in a gas chromatography heating oven (Hewlett Packard) under nitrogen atmosphere. Solvents and chemical reagents were delivered to the bottom ends of the channels using nitrogen pressure (50 psi). Solvents and reagents were removed by vacuum.

The reactions in the two derivatization steps is described by the following reaction schemes:

(1) —Si—OH+(EtO)$_3$Si—H→Si—O—Si—H+3EtOH (2) —Si—H+CH$_2$=CH—R—→Si—CH$_2$—CH$_2$—R where R=—OC(=O)CH$_2$C(CH$_3$)=CH$_2$ In the first derivatization step, a silicon-hydride monolayer was formed by washing the channels with dioxane, and then treating them with a steady flow of 1.0 M solution of TES in dioxane at 90° C. for 60 minutes. Constant flow was necessary to prevent reagent deposition and clogging of the channels. The hydride-modified surface was then washed sequentially at room temperature with several volumes of dioxane, tetrahydrofuran (THF), and then toluene. Toluene was maintained over the channels for the next step.

The hydride-modified surface was washed with dry toluene. A mixture of 25 mL pure allyl methacrylate plus 25 mL toluene was mixed with 70 $\mu$L of 10 mM Spiers catalyst (hexachloroplatinic acid in 2-propanol) and heated to 60–70° C. for one hour before being flushed through the channels at 100° C. for 5 to 24 hours. This allyl methacrylate treatment procedure was repeated one more time, after which the surface was washed successively with toluene and THF.

Immobilines were attached to the surface allyl methacrylate groups in the IEF region of the separation cavity as follows. A gradient of Immobilines was delivered to the coated region from the bottom of the electrophoresis apparatus via a quaternary HPLC pump connected to the inlet of a delta-shaped delivery element. The gradient was generated using two solutions, A and B.

|  | Amount ($\mu$L) |
|---|---|
| Solution A |  |
| Immobiline pK 3.6 | — |
| Immobiline pK 4.6 | 105 |
| Immobiline pK 6.2 | 46 |
| Immobiline pK 7.0 | 449 |
| Immobiline pK 8.5 | 144 |
| Immobiline pK 9.3 | 330 |
| acrylamide (10% w/v) | 433 |
| water | 3496 |

-continued

| | Amount (μL) |
|---|---|
| glycerol | 750 |
| Solution B | |
| Immobiline pK 3.6 | 413 |
| Immobiline pK 4.6 | — |
| Immobiline pK 6.2 | 171 |
| Immobiline pK 7.0 | 34 |
| Immobiline pK 8.5 | 126 |
| Immobiline pK 9.3 | — |
| acrylamide (10% w/v) | 216 |
| water | 1771 |
| glycerol | 144 |

Solutions A and B were degassed and the pH was adjusted to 7.0 by adding 2 drops of 0.1 M HCl to solution A and 2 drops of 0.1 M NaOH to solution B. The electrophoresis apparatus was first filled from the bottom with water at a flow rate of 0.1 mL/min, to minimize capillary action. Next, 5.5 μL each of TEMED and APS were added to solution A, and 3 μL each of TEMED and APS were added to solution B. The gradient was then started, going from 0% to 100% A over 2.3 min. at a flow rate of 0.3 mL/min. At the end of the gradient, flow was stopped briefly, after which a solution of 40% glycerol/0.05% bromphenol blue (gradient-chasing solution) was pumped in at 0.1 mL/min. When the front of the dye solution reached the bottom of the plates, the flow was stopped, and the Immobiline coating reaction was allowed to proceed for 5 hours with the plates in an upright position. The Immobiline mixture was then removed, and the apparatus was filled with water. The resulting Immobiline gradient was sufficient to create a substantially linear pH gradient spanning pH 3 to 9, from the top to the bottom of the channel region.

Although the invention has been described with respect to particular embodiments and examples for purposes of illustration, it will be appreciated that various modifications can be made without departing from the scope and spirit of the invention.

What is claimed is:

1. A two-dimensional electrophoresis system for separating components within a sample, comprising
   (a) an electrophoresis plate assembly which defines:
      (i) a sample separation cavity, having an upper portion and a lower portion, and bounded by opposing major first and second plate surfaces, each having a defined width and length, which are spaced apart by an interfacial distance substantially shorter than said width and length, said cavity comprising (1) a first electrophoresis region within said upper portion, adapted to perform charge and/or size-based electrophoresis in a first dimension, and occupied bv a flowable, noncrosslinked aqueous separation medium, and (2) a second electrophoresis region within said lower portion, below and abutting the first electrophoresis region, adapted to perform electrophoresis in a second dimension, in a direction substantially perpendicular to said first dimension, containing a plurality of elongate separation channels defined by one of said plate surfaces and substantially perpendicular to said first dimension, and occupied by a flowable, noncrosslinked aqueous medium. and
      (ii) a sample loading port in fluid communication with said first region, for introducing a sample into said first electrophoresis region,
   (b) electrode means for generating a first voltage potential across the first electrophoresis region, and
   (c) electrode means for generating a second voltage potential across said the second electrophoresis region, wherein said flowable aqueous media occupying said first and second regions are in physical communication.

2. The system of claim 1, wherein said media are such that the rates of migration of sample components in the second dimension depend on sample properties that are different from the sample properties that determine sample migration rates in the first dimension.

3. The system of claim 1, wherein at least one of said flowable media includes a plurality of linear polyacrylamide molecules.

4. The system of claim 3, wherein the flowable medium occupying said first region includes a plurality of linear polyacrylamide molecules.

5. The system of claim 1, where the second electrophoresis region contains an isoelectric focusing region containing a continuous $pK_a$ gradient immobilized on at least one of said major opposing plate surfaces.

6. The system of claim 5, wherein said gradient comprises a coating of buffering molecules covalently attached to at least one of said opposing plate surfaces.

7. The system of claim 1, wherein said flowable medium occupying said second region is a low ionic strength aqueous buffer.

8. The system of claim 1, wherein said second region contains at least 30 separation channels.

9. The system of claim 1, wherein said plate assembly further defines a liquid loading region abutting said cavity.

10. The system of claim 9, wherein said liquid loading region abuts said first electrophoresis region.

11. The system of claim 1, wherein said loading port is joined to said first region via an elongate sample transport channel.

12. A two-dimensional method for separating one or more components of a sample mixture by planar isoelectric focusing, said method comprising
   (a) providing an electrophoresis plate assembly defining a planar sample separation cavity, bounded by opposing major first and second plate surfaces, which includes
      (i) a first electrophoresis region, containing a first flowable, noncrosslinked aqueous separation medium, and adapted to perform charge and/or size-based electrophoresis in a first dimension, and
      (ii) a second electrophoresis region, abutting the first electrophoresis region, containing (1) a second flowable, noncrosslinked aqueous medium in physical communication with said first medium, (2) a continuous $pK_a$ gradient immobilized on at least one of said plate surfaces, and (3) a plurality of elongate separation channels defined by at least one of said plate surfaces. substantially perpendicular to said first dimension, said second region being adapted to perform isoelectric focusing in a second dimension, in a direction substantially perpendicular to said first dimension,
   (b) applying said sample mixture to said first region,
   (c) applying a first voltage potential across the first region, under conditions effective to cause said sample components to migrate across the region, such that different components become separated at least partially on the basis of size,
   (d) applying a second voltage potential across the second region, such that said migrated sample components migrate into the second region, in a direction substantially perpendicular to said first dimension, and become separated on the basis of their isoelectric points.

13. The method of claim 12, wherein the $pK_a$ gradient defines a $pK_a$ range of about 4 to 10.

14. The method of claim 12, wherein said $pK_a$ gradient comprises a coating of buffering molecules covalently attached to at least one of said opposing plate surfaces.

15. The method of claim 14, wherein said buffering molecules are covalently attached to said channels.

16. The method of claim 12, wherein said second region contains at least 30 separation channels.

17. The method of claim 12, wherein said flowable medium occupying said second region is a low ionic strength aqueous buffer.

18. The method of claim 12, wherein the flowable medium occupying said first region includes a plurality of linear polyacrylamide molecules.

19. The method of claim 12, wherein the sample components are polypeptides.

20. The method of claim 12, wherein the sample components include a detectable label.

21. The method of claim 12, further comprising detecting the locations of the separated sample components following step (d).

22. The method of claim 12, further comprising collecting at least one of the separated sample components following step (d).

23. The method of claim 12, wherein said plate assembly further defines a liquid loading region abutting the cavity and defined by said first and second plate surfaces.

24. The method of claim 23, wherein said liquid loading region abuts the first electrophoresis region.

25. The method of claim 23, wherein said $pK_a$ gradient is prepared by (a) coating said opposing plate surfaces in the vicinity of said second region, with binding groups effective to covalently bind said buffering molecules;

(b) providing first and second gradient solutions containing, respectively, a plurality of low $pK_a$, buffering molecules and a plurality of high $pK_a$ buffering molecules;

(c) orienting said plate assembly vertically, such that said liquid loading region is situated below said sample separation cavity;

(d) transferring a mixture of said gradient solutions into said liquid loading region and thence into said cavity, such that a progressively increasing proportion of said second gradient solution is included in said mixture during said transferring, (e) allowing said mixture to react with said binding groups, and (f) removing said mixture from said cavity.

26. The method of claim 25, wherein the mass density of said second gradient solution is greater than that of said first gradient solution.

* * * * *